(12) United States Patent
Davies

(10) Patent No.: US 6,790,249 B2
(45) Date of Patent: Sep. 14, 2004

(54) APPARATUS AND METHOD FOR SCREENING PEOPLE AND ARTICLES TO DETECT AND/OR DECONTAMINATE WITH RESPECT TO CERTAIN SUBSTANCES

(75) Inventor: John H. Davies, Mississauga (CA)

(73) Assignee: Smiths Detection-Toronto Ltd., Mississauga (CA)

(*) Notice: Subject to any disclaimer, the term of this patent is extended or adjusted under 35 U.S.C. 154(b) by 0 days.

(21) Appl. No.: 10/127,694

(22) Filed: Apr. 23, 2002

(65) Prior Publication Data

US 2003/0041573 A1 Mar. 6, 2003

Related U.S. Application Data

(63) Continuation-in-part of application No. 09/389,019, filed on Sep. 2, 1999, now Pat. No. 6,375,697.

(51) Int. Cl.[7] .................. B01D 34/14; B01D 53/24; G01N 1/22

(52) U.S. Cl. .................. 55/340; 55/385.2; 55/467; 55/DIG. 34; 96/413; 96/417; 454/187; 454/230; 73/23.2

(58) Field of Search .................. 55/340, 385.2, 55/467, DIG. 34; 96/413, 417; 454/187, 230; 73/23.2

(56) References Cited

U.S. PATENT DOCUMENTS

| | | | |
|---|---|---|---|
| 4,896,547 A | | 1/1990 | Arney et al. |
| 4,987,767 A | | 1/1991 | Corrigan et al. |
| 5,915,268 A | * | 6/1999 | Linker et al. ............ 73/23.2 |
| 6,073,499 A | * | 6/2000 | Settles ............ 73/864.81 |

* cited by examiner

Primary Examiner—Robert A. Hopkins
(74) Attorney, Agent, or Firm—Bereskin & Parr

(57) ABSTRACT

Improvements are provided to enable an air-curtain portal to be used for the triage and decontamination of persons who may have been exposed to toxic gas vapour or particulate material.

72 Claims, 2 Drawing Sheets ated in liquid form, and the liquids have effectively low
APPARATUS AND METHOD FOR SCREENING PEOPLE AND ARTICLES TO DETECT AND/OR DECONTAMINATE WITH RESPECT TO CERTAIN SUBSTANCES This application is a continuation-in-part of application Ser. No. 09/389,019, filed Sep. 2, 1999, now U.S. Pat. No. 6,375,697.

FIELD OF THE INVENTION

This invention relates to both an apparatus for and method of screening people and articles to detect exposure and/or to decontaminate with respect to toxic materials, such as condensible gases and vapours and liquid or solid particles originating from industrial accidents or chemical warfare.

BACKGROUND OF THE INVENTION

Rapid screening techniques are required to quickly identify people who may have been exposed to toxic emissions, notably either from chemical warfare gases and vapours or chemicals spilled or accidentally formed from industrial accidents. Often these substances are released or disseminated in liquid form, and the liquids have effectively low boiling points such that the vapours are readily emitted.

Following a chemical warfare agent attack, for example, numerous people could be contaminated, as, for example, in crowded metropolitan underground rail systems. Since nerve and chemical warfare agents are extremely toxic, quick response and remedial action is essential. If liquid agents were disseminated into closed areas, the contamination could be very high. Great care must therefore be taken to ensure that in a mixed population of victims or potential victims, those who are contaminated are quickly separated from those who are not.

In the Tokyo Metropolitan Rail attack, sarin was used and the First Responders (i.e., emergency personnel such as Fire, Police or ambulance staff, who first arrived at the scene) were unable to separate contaminated from uncontaminated people. As a consequence, victims whose clothing had been contaminated with the sarin became sources of reliberation of the vapours, which then cross-contaminated people who were originally unaffected. Thus, the casualties from the attack were greatly multiplied.

It is most desirable, therefore, to develop a quick screening system where individuals could pass through a walk-through portal, similar to Walk-Through Metal Detectors (WTMD) used in airports for screening passengers for concealed weapons. Just as WTMD systems detect the presence of metal objects, the inventor has realized that a similar screening system could be used to detect the presence of chemical agents. There is a need for easily deployed walk-through portal systems provided with air jets that can air brush people and speedily process possible victims on a walk-through basis.

Linker et al in U.S. Pat No. 5,915,268, Settles in U.S. Pat. No. 6,073,499, Arney et al in U.S. Pat. No. 4,896,547 and Corrigan et al. in U.S. Pat. No. 4,987,767, teach that a curtain using flowing air, or other gas, can quickly thermally desorb high vapour pressure materials from the skin and/or clothing of persons, and, further, that such air curtains can be integrated into portals which can be used to screen persons for the presence of a wide variety of materials, most commonly explosives and drugs of abuse. The present invention provides improvements to prior art portals to extend their use to the triage and decontamination of persons who, as the result of chemical warfare, terrorist attack, or industrial or transportation accident, may have been exposed to toxic substances which have become attached to their skin and clothes, thereby prolonging their exposure and increasing the probability of serious injury.

SUMMARY OF THE INVENTION

A walk-through portal can include a plenum which can deliver a high volume flow of warm air over the person being processed. The person walks into the portal and executes a 90' turn so that the air jets, preferably heated, can blow over the front and back areas of their body. Typically, the person remains in the examination zone for about 12 seconds, and is swept by about 2,000 L of air. An exhaust system collects the warm air into a plenum containing a filter. Any chemical on skin or clothing is liberated and passes as either particles, droplets or vapour into the plenum for subsequent removal by the filtering system. An analytical instrument such as an ion mobility spectrometer, is used to make chemical measurements on the air flow exhausted through the plenum prior to filtering. However, many other techniques exist. An enrichment process can allow agents to be removed from the high volume air flow so as to be transferred into a much lower air flow compatible with instruments such as an IMS detector. Other instruments can be used to monitor the effluent such as fast gas chromatographs, IR analyzers, electrochemical cells and other such devices according to their analytical capabilities and speed of response for the analytes of interest. Shutting off the main air flow and heating the filter in a much lower air flow can provide an enrichment process and allow agents to be detected at lower levels. Such devices can be provided in a portable form such that they may be readily transported from site to site and quickly reassembled where chemical terrorism acts or industrial accidents may have occurred. Alternatively such portals can be permanently installed at critical sites. Such a portal can also be optimized for detection of contraband substances.

In actual operation, especially where large numbers of individuals may need to be processed, speed is of essence and a number of such prescreening warm air only portals could be provided. The preliminary processing involves basic air decontamination; the individuals could be subsequently screened through a second portal which incorporates the chemical measurement means to check if decontamination was successful. Where the number of victims are few, a single portal can perform the functions of decontamination and contamination monitoring.

The portals could be constructed as portable devices or "knock-down" kits, allowing for ease of transport and rapid assembly at the site of the chemical release. Evidently, such portals could be permanently constructed for us in chemical plants or military installations where dangerous chemical materials are stored, handled, processed or positioned. Additionally, such portals could be used as security screens at airport check points.

In accordance with a first aspect of the present invention, there is provided a walk-through portal for at least one of detection of a predetermined substance on a subject and decontamination of a subject from a predetermined substance, the walk-through portal comprising:

an enclosure defining an examination zone and being substantially open on at least one side, to permit a subject readily to enter and to exit the examination zone;

a closure means for substantially closing off the examination zone from the exterior;

an inlet into the examination zone and an outlet from the examination zone; and a pump for pumping a gas through the inlet into the examination zone, over a subject to entrain at least one of vapours, and particulates from such substance, and out through the outlet.

The portal preferably includes at least one flexible screen, closing off the examination zone. More preferably, the walk-through portal is open on opposite sides thereof, to enable a subject to walk into the examination zone from one side and out from the examination through the other side, and the walk-through portal further includes flexible screens on both sides, closing off the examination zone.

Advantageously, the portal includes an output decontamination filter connected to the outlet from the examination zone, for ensuring that gas exhausted into the atmosphere is free from any contaminating substance and/or an inlet filter, mounted between the inlet and the examination zone, for filtering gas flowing into the examination zone.

Preferably, the walk-through portal includes an analyzer, connected to the outlet, for taking a sample of gas flowing through the outlet, whereby the analyzer determines the presence of said substance in the gas flowing through the outlet and/or a detection instrument connected to the inlet, for monitoring gas flowing into the examination zone for presence of contamination.

Instead of an open system, the portal can include a recirculation duct connected between the outlet and the inlet and a filter mounted in the recirculation duct, for cleaning gas exhausted from the examination zone of any contaminating substance, before the gas is recirculated back through the inlet into the examination zone.

In either version, the portal can include a supply of a decontamination agent, connected to the recirculation duct, downstream from the filter, for supply of a decontamination agent for one of neutralization, destabilizing and breaking down said substance.

An indicator can be connected to the analyzer and is operable to provide an indication as to whether a subject is or is not contaminated with said substance. A connection can be provided between the analyzer and the pump, for turning off the pump, after a predetermined period of time, when it is determined that said substance is not present, indicative that subject is not contaminated.

Another aspect of the present invention provides a device, for at least one of detection of a predetermined substance on an article and 10 decontamination of an article from a predetermined substance, the device comprising:

an enclosure defining the examination zone, the enclosure being openable for insertion and removal of an article and being closable to close off the examination zone from the exterior;

an inlet into the examination zone and an outlet from the examination zone;

a pump for pumping a gas through the inlet into the examination zone, over the article to entrain at least one of vapours and particulates of said substance, and out through the outlet; and an analyzer connected to the outlet, for sampling gas flowing through the outlet, whereby the analyzer determines the presence of said substance, indicative of contamination of the article by said substance.

Yet another aspect of the present invention provides a method of effecting at least one of detection of a substance on a subject and decontamination of the subject, the method of comprising the steps of:

(1) enclosing the subject in an examination zone substantially closed off from the exterior;

(2) passing gas into the examination zone, to entrain at least one of vapours and particulates of said substance; and (3) withdrawing gas from the examination zone.

The present invention further improves portals according to the prior art by adding at least one of, a breathing mask with a clean air supply so that the subject will not inhale toxic materials liberated from their clothing and skin, one or more flexible transparent screens over the entrance and exit of the portal to limit air exchange without inducing claustophobic symptoms in the person in the examination zone, a supply of decontamination agent to neutralize toxic materials, an analyzer to monitor the inlet air for contamination, a camera and an automated image analysis system to examine the person for miosis, or other symptoms of injury by toxic substances.

The most rapid and efficient route of ingestion of toxins is by inhalation. While air curtains are well suited to the removal of superficial toxic material, they may produce dangerous concentrations in the air being inhaled by the person being decontaminated. The improvements according to the present invention provide a breathing mask to supply pure air to a person undergoing examination and decontamination in a portal. Advantageously, this breathing mask can also be used to supply a therapeutic gas, such as oxygen. Many airborne toxins compromise respiratory function, and administration of oxygen is a recognised first-aid proceedure in cases of known or suspected exposure to airborne toxics.

Toxics made airborne during examination and decontamination could be a hazard not only to the person in the portal, but also to those awaiting processing and to emergency workers. While the design of prior art portals seeks to minimize air exchange with the outside environment in the interests of achieving the maximum concentrations of analyte in the sample airstream, this may not be sufficient to protect persons in the vicinity of a portal being used for decontamination, where the concentrations of evolved material are likely to be higher than in the contraband detection application. The obvious remedy of providing conventional doors on a portal has the disadvantages of slowing throughput and of inducing claustrophobic panic, particularly under the stress of an emergency. Accordingly, the improvements of the present invention provide the entrance and exit of the portal with flexible screens consisting of vertically-disposed ribbons of clear flexible material suspended from the lintels. The ribbons are flexible, slightly weighted at the bottom, and have a slight overlap of their vertical edges, so that they provide a significant barrier to gas exchange and yet even a child can easily walk through them, and this ease, combined with their transparency, makes closures of this type minimally threatening, particularly to chidren and the elderly.

Portals of the prior art provide an air flow which removes material from the skin and clothes of the person being processed. The improvements according to the present invention provide for the enhancement of decotamination by addition to the air stream, on the inlet side, of a gas, vapour, or particulate material which reacts with and neutralizes the toxic material to which the victim has been exposed.

For some time after a deliberate or accidental release of toxic material, clouds of toxics may continue to drift around the area. If such a cloud were to be ingested into the examination zone of a portal it would compomise the examination and imperil the health of the person being examined. Portals of the prior art are not designed to deal with impurities or hazardous materials in the input air. The improvements according to the present invention provide an analyzer, such as an ion mobility spectrometer, to monitor the inlet air and generate an audible, visible or other alarm if contamination is detected.

Portals of the prior art typically include sensors which could be programmed to indicate the level of contamination, but they do not provide any indication of the degree to which potential victims have been affected by their exposure. This information can be vital to triage in emergency situations, where large numbers of persons may be at risk, and highly-trained medical help and treatment resources are likely to be in limited supply or only obtainable at distant sites. The improvements according to the present invention provide a camera and automated image analysis system to examine the person for miosis, or other symptoms of injury by toxic substances.

BRIEF DESCRIPTION OF THE DRAWINGS

For a better understanding of the present invention and to show more clearly how it may be carried into effect, reference will now be made, by way of example to the accompanying drawings, in which.

DETAILED DESCRIPTION OF THE INVENTION

Figure 1:
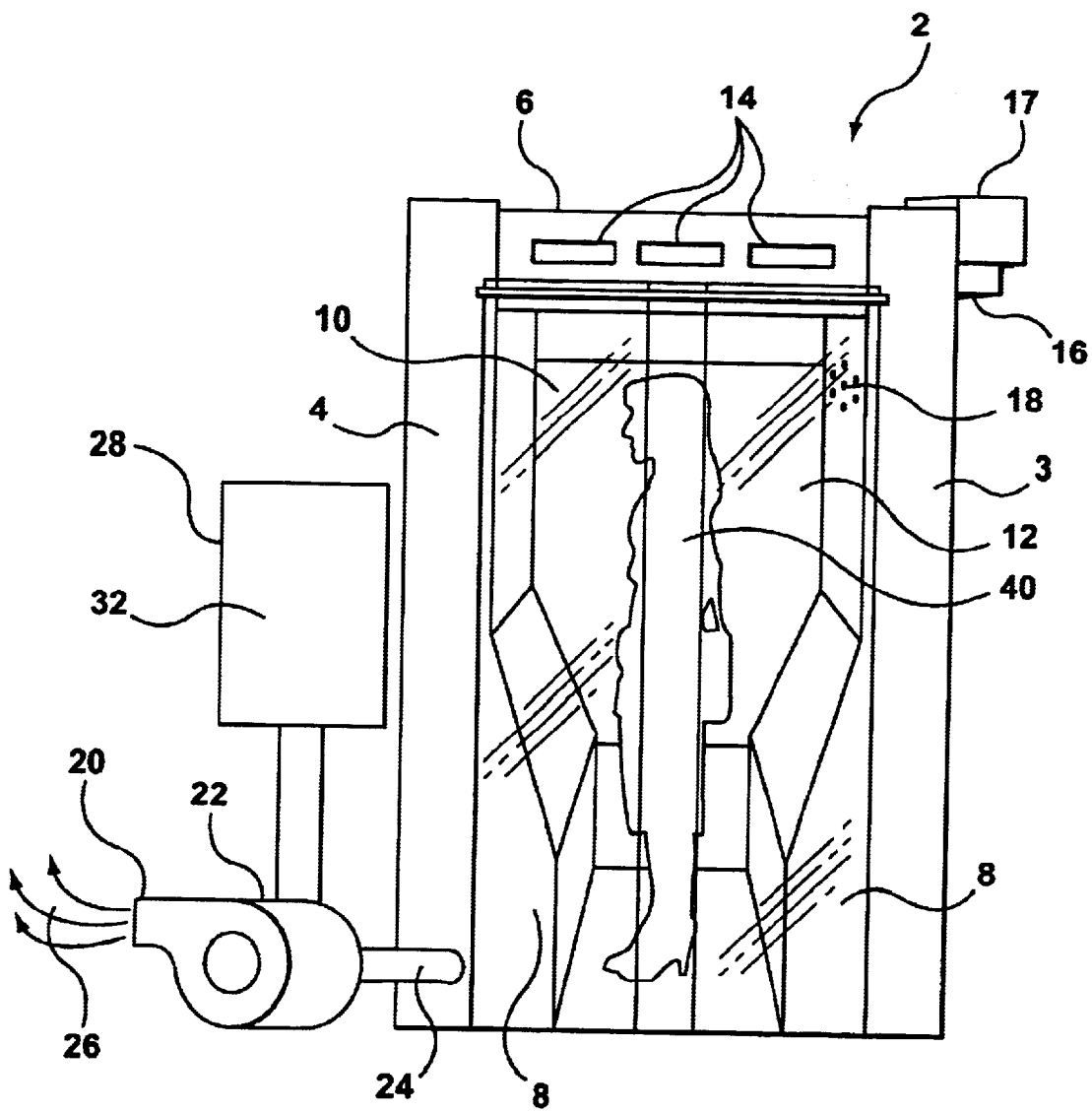
FIG. 1 is a walk-through portal in accordance with the prior art.

Referring first to FIG. 1, apparatus includes a main portal structure 2, which comprises two vertical side members 3, 4 and a crosspiece 6 at the top. The vertical side members 3, 4 are generally vertical and parallel at the top thereof, and towards the bottom, include trapezoidal sections 8 shaped to match the human silhouette, ensuring efficient airflow and collection. The portal illustrated is one-sided, i.e. "walk-in" rather than "walk-through". The rear wall can have a solid portion below a window; either walk-in or walk-through versions are possible, but having a solid wall simplifies control of air flow and aids efficient sampling. Note that, in its broadest since, the term "walk-through" is used in the claims to encompass a partial open on just one side and a partial open on both sides.

The vertical side members 3, 4 together with the crosspiece 6 define an examination zone 10. To close off this examination zone 10, flexible screens, indicated schematically at 12 are provided at the front and back of the apparatus, i.e., above and below the plane of FIG. 1.

In the crosspiece 6, inlets 14 are provided for ambient air. The inlets 14 are connected to a filter canister 16, which in turn is connected to a plurality of jet orifices 18. Often a heater 17 for preheating the air is provided downstream from filter 16. To draw air through the examination zone 10, a blower 20 is connected by an output decontamination filter 22 to an outlet 24, opening near the bottom of the examination zone 10. The orifices 18 are provided towards the top of the examination zone 10. The exhaust stream from the blower 20 is indicated at 26. An analyzer 28 having an indicator 32 is connected to the outlet 24, immediately upstream from the decontamination filter 22 in order to detect the prescence of substances of interest. Here, an ion mobility spectrometer is shown. In some cases, the inlet filter 16 is omitted and the output of the blower is connected via a recirculation duct (not shown) to the orifices 18.

In operation the person to be processed enters the examination zone 10 and makes a 90° turn. The blower is then activated and the outside ambient air is drawn into the portal through the inlet 14 and filtered through the filter canister 16. The air is then heated by the heater 17, if present, and is drawn into the interior volume, or examination zone 10 through the series of jet orifices 18. The air pressure and flow are sufficient to levitate solid particles off the subject 40 and/or provide sufficient heat input to the toxic materials resident on the surface of the subject or victim 40 and his/her clothing, to cause their evaporation into the exhaust flow. The action of the blower 20 draws the exhaust flow 15 through the outlet duct 24 and decontamination filter 22. As the flow passes through the duct 24 it is monitored by the analyzer 28. If a clear indication is given, then the person 40 is told to exit the device. If a warning is given, then the flow is continued until the indication changes to clear or a preset time has passed. If the preset time is insufficient to achieve decontamination, then the person's status in the triage is advanced and they are diverted to appropriate secondary treatment.

Figure 2:
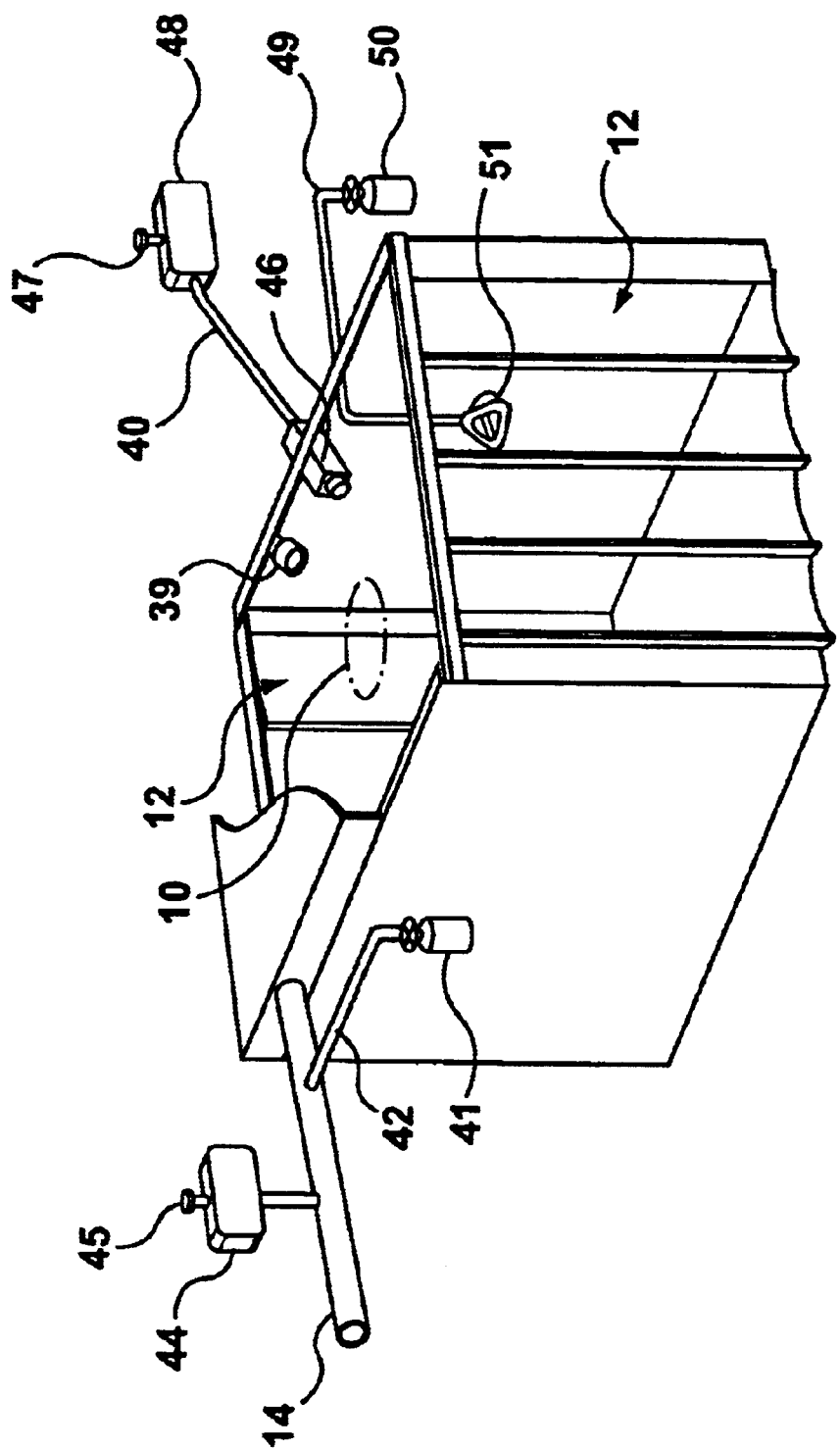
FIG. 2 shows schematically a perspective view of additional components of the walk-through portal according to the present invention.

Turning to FIG. 2, this shows schematically the improvements according to the present invention which extend the use of prior art portals to the triage and decontamination of persons who may have been exposed to toxic materials. In FIG. 2, the upper portions of the portal have been removed to show interior features. To close off the examination zone 10, flexible screens, indicated schematically at 12 are provided at the front and optionally, at the back of the apparatus. The flexible screens 12 could be simple plastic strips or sheets, which are preferably easily removable for decontamination. For a simple installation, screens, or a screen, could be provided on just one side, although this would require a person to enter and exit from the same side. In use, a person enters the portal by walking through flexible screens 12. If a person has bags or luggage, these can be checked with the individual, if small, or subject to a separate check. Once the person is within the examination zone 10, the flexible screens 12 effectively, efficiently and quickly seal the zone 10.

Where appropriate, a supply of decontamination agent can be provided. When contamination is detected the supply 41 is activated to supply the decontaminating agent via the conduit 42 to the inlet plenum 14 and hence to the examination zone 10. The agent from the supply 41 can be such as to either break down, neutralize or destabilize the toxic chemical. Although not shown in FIG. 2, it will be obvious to those skilled in the art that, in portals where the output of the blower is recirculated, the conduit 42 will be connected to the recirculation duct.

An analyzer 44 furnished with an alarm 45 is connected to the inlet plenum 14 in order to monitor the air being drawn into the examination zone 10 for contamination. The analyzer 14 is advantageously an Ion Moboility Spectrometer.

Referring again to FIG. 2, a supply of pure air 50 is connected by a conduit 49 which passes through the wall of the examination zone 10 to a breathing mask 51. Advantageously, the portion of the conduit 49 which is within the zone 10 is made of a flexible and extensible material so that a person of any size may comfortably use the breathing mask 51.

To assist in assessment of the person being processed, a video camera 46 and lighting system 39 is provided. The camera 46 accquries electronic images of the person's face which are transferred by the cable 40 to an automatic image processor 48 which activates an alarm 47 if symptoms of injury are detected. In an alternative embodiment, the processor 48 is replaced by telemetric means which relays the image stream to a distant site for display and diagnosis by skilled personnel. It will be obvious that the telemetric means can be bi-directional and can allow the diagnostician at the remote site to control the alarm means 47 and thereby convey instructions to personnel on the scene of the emergency. Advantageously, additional cameras and lights (not shown) can be positioned within the zone 10 so as ensure that an appropriate view of the person being processed is available independently of their size or their orientation within the zone.

Several applications are contemplated for the improved walk-through portal of the present invention, including:

Transportable Decontamination Portals for First Responders and other emergency response teams. These units would be configured to be quickly set up. In cases of terrorist attacks and chemical toxic releases, the fastest possible response to provide decontamination and provision of uncontaminated air flow is vital. For a portable installation, the portal should be constructed in modular form of lightweight materials, such as plastics, which render easy transportation, and quick stripdown and reassembly, thereby facilitating movement to different sites.

Fixed Portal systems could be permanently established in key facilities or in areas where dangerous and volatile chemicals are stored, handled and analyzed, e.g. major manufacturing installations and the like.

Other aspects of this invention are shown in co-pending application, Ser. No. 09/389,019 and are hereby incorporated by reference.

What is claimed is:

1. A decontamination system for removing a substance from a subject, the decontamination system comprising:
   a structure for surrounding the subject;
   an inlet for allowing a gas to enter the structure;
   an outlet for allowing the gas to exit the structure;
   a pump for pumping the gas through the inlet, into the structure, around the subject, and out through the outlet, thereby removing at least one of substance particles and substance vapours from the subject; and
   an inlet analyzer for monitoring the inlet air for contamination.

2. The system of claim 1, further comprising an alarm that is activated if the inlet analyzer detects that the inlet air is contaminated.

3. The system of claim 2, further comprising a neutralizing unit for treating the gas in the system with an agent that neutralizes the substance.

4. The system of claim 3, wherein the neutralizing unit treats the gas before the gas is pumped over the subject.

5. The system of claim 4, further comprising a camera for monitoring the subject for any signs of ill effects arising from exposure to the substance.

6. The system of claim 5, further comprising an automated image analysis system for identifying symptoms in the subject arising from exposure to the substance.

7. The system of claim 6, wherein the automated image analysis system identifies symptoms of miosis in the subject.

8. The system of claim 7, further comprising a breathing mask to supply air to the subject while the subject is being decontaminated.

9. The system of claim 8, further comprising a therapeutic gas provider for supplying a therapeutic gas to the subject via the breathing mask.

10. The system of claim 9, further comprising:
    an entrance for allowing the subject to enter the structure and an exit for allowing the subject to exit the structure; and
    at least one screen over the entrance and the exit to limit air exchange between the inside of the structure and the outside of the structure.

11. The system of claim 10, wherein the screen is transparent.

12. The system of claim 11, wherein the screen is flexible.

13. The system of claim 12, wherein the entrance and the exit allow the subject to walk into the structure from one side and out from the structure through an opposite side.

14. The system of claim 13, further comprising an output decontamination filter, mounted at the outlet, for removing contaminants from the gas exiting the structure.

15. The system of claim 14, further comprising an inlet filter, mounted at the inlet, for removing contaminants from the gas entering the structure.

16. The system of claim 15, further comprising an outlet analyzer for monitoring the outlet air for contamination.

17. The system of claim 16, further comprising an outlet alarm that is activated if the outlet analyzer detects that the outlet air is contaminated.

18. The system of claim 17, further comprising a connection between the outlet analyzer and the pump, for turning off the pump, after a predetermined period of time, when it is determined that contaminants are not present in the gas exiting the structure, indicative that the subject is not contaminated.

19. The system of claim 18, further comprising a recirculation duct connected between the outlet and the inlet and a filter mounted in the recirculation duct for ridding the gas that exits the outlet of any contaminants before the gas is recirculated back through the inlet Into the structure.

20. The system of claim 19, further comprising a recirculation duct analyzer connected to the recirculation duct for taking a sample of the gas exiting the structure, upstream from the filter, whereby the recirculation duct analyzer can determine the presence of contaminants in the gas.

21. The system of claim 20, further comprising a heater mounted upstream of the inlet for heating gas flowing to the inlet.

22. A decontamination method for removing a substance from a subject, the decontamination method comprising:
    surrounding a subject in a structure;
    pumping gas through an inlet into the structure;
    directing the gas to flow around the subject to entrain at least one of substance particles and substance vapours, thereby decontaminating the subject;
    expelling the gas, along with any entrained contaminants, from the structure through an outlet; and
    analyzing with an inlet analyzer the inlet air for contamination.

23. The method of claim 22, further comprising activating an alarm if the inlet analyzer detects that the inlet air is contaminated.

24. The method of claim 23, further comprising treating the gas in the system with an agent that neutralizes the substance.

25. The method of claim 24, wherein the step of treating includes treating the gas before the gas is pumped over the subject.

26. The method of claim 25, further comprising monitoring the subject with a camera for any signs of ill effects arising from exposure to the substance.

27. The method of claim 26, further comprising identifying symptoms in the subject arising from exposure to the substance with an automated image analysis system.

28. The method of claim 27, wherein the step of identifying includes identifying symptoms of miosis with the automated image analysis system.

29. The method of claim 28, further comprising supplying air to the subject with a breathing mask while the subject is being decontaminated.

30. The method of claim 29, further comprising supplying a therapeutic gas to the subject via the breathing mask.

31. The method of claim 30, further comprising:
providing an entrance for the subject to enter the structure and an exit for the subject to exit the structure; and
limiting air exchange between the inside of the structure and the outside of the structure with at least one screen.

32. The method of claim 31, wherein the screen is transparent.

33. The method of claim 32, wherein the screen is flexible.

34. The method of claim 33, further comprising allowing the subject to walk into the structure from one side via the entrance and out from the structure through an opposite side via the exit.

35. The method of claim 34, further comprising removing contaminants from the gas exiting the structure with an output decontamination filter mounted at the outlet.

36. The method of claim 35, further comprising removing contaminants from the gas entering the structure with an Inlet filter mounted at the inlet.

37. The method of claim 36, further comprising monitoring the outlet air for contamination with an outlet analyzer.

38. The method of claim 37, further comprising activating an outlet alarm if the outlet analyzer detects that the outlet air is contaminated.

39. The method of claim 38, further comprising:
electrically connecting the outlet analyzer and the pump;
determining that contaminants are not present in the gas exiting the structure, which indicates that the subject is not contaminated; and
after the step of determining, turning off the pump.

40. The method of claim 39, further comprising:
connecting the outlet and the inlet with a recirculation duct; and
ridding the gas that exits the outlet of any contaminants with a filter mounted in the recirculation duct before the gas is recirculated back through the inlet into the structure.

41. The method of claim 40, further comprising taking a sample of the gas exiting the structure, upstream from the filter, with a recirculation duct analyzer connected to the recirculation duct, whereby the recirculation duct analyzer can determine the presence of contaminants in the gas.

42. The method of claim 41, further comprising heating gas flowing to the inlet with a heater mounted upstream of the inlet.

43. A portal for at least one of detection of a substance on a subject and decontamination of a subject from a substance, the portal comprising:
an enclosure for enclosing the subject in an examination zone;
a gas inlet into the examination zone and a gas outlet from the examination zone;
a pump for pumping a gas through the gas inlet into the examination zone, for directing the gas around the subject in the examination zone to entrain at least one of substance vapours and substance particulates, and for expelling the gas, along with any entrained contaminants, through the gas outlet; and
an inlet analyzer to monitor the inlet gas for contamination.

44. The portal of claim 43, further comprising an alarm that is activated if the inlet analyzer detects that the inlet air is contaminated.

45. A portal for at least one of detection of a substance on a subject and decontamination of a subject from a substance, the portal comprising:
an enclosure for enclosing the subject in an examination zone;
a gas inlet into the examination zone and a gas outlet from the examination zone;
a pump for pumping a gas through the gas inlet into the examination zone, for directing the gas around the subject in the examination zone to entrain at least one of substance vapours and substance particulates, and for expelling the gas, along with any entrained contaminants, out the gas outlet; and
a camera for monitoring the subject for any signs of ill effects arising from exposure to the substance.

46. The portal of claim 45, further comprising an automated image analysis system for identifying symptoms in the subject arising from exposure to the substance.

47. A method for at least one of detecting a substance on a subject and decontaminating a subject from a substance, the method comprising:
enclosing the subject in an examination zone;
pumping gas through an inlet into the examination zone;
directing the gas to flow around the subject to entrain at least one of substance particles and substance vapours, thereby decontaminating the subject; and
expelling the gas, along with any entrained contaminants, out of the examination zone through an outlet; and
monitoring the inlet gas for contamination with an inlet analyzer.

48. The method of claim 47, further comprising activating an alarm if the inlet analyzer detects that the inlet air is contaminated.

49. A method for at least one of detecting a substance on a subject and decontaminating a subject from a substance, the method comprising:
enclosing the subject in an examination zone;
pumping gas through an inlet into the examination zone;
directing the gas to flow around the subject to entrain at least one of substance particles and substance vapours, thereby decontaminating the subject; and
expelling the gas, along with any entrained contaminants, out of the examination zone through an outlet; and
monitoring the subject with a camera for any signs of ill effects arising from exposure to the substance.

50. The method of claim 49, further comprising identifying symptoms in the subject arising from exposure to the substance with an automated image analysis system.

51. A decontamination system for removing a substance from a subject, the decontamination system comprising:
a structure for surrounding the subject;
an inlet for allowing a gas to enter the structure;
an outlet for allowing the gas to exit the structure;
a pump for pumping the gas through the inlet, into the structure, around the subject, and out through the outlet, thereby removing at least one of substance particles and substance vapours from the subject; and
a neutralizing unit for treating the gas in the system with an agent that neutralizes the substance.

52. The system of claim 51, wherein the neutralizing unit treats the gas before the gas is pumped over the subject.

53. The system of claim 52, further comprising a camera for monitoring the subject for any signs of iii effects arising from exposure to the substance.

54. The system of claim 53, further comprising an automated image analysis system for identifying symptoms in the subject arising from exposure to the substance.

55. The system of claim 51, further comprising:

an entrance for allowing the subject to enter the structure and an exit for allowing the subject to exit the structure; and at least one screen over the entrance and the exit to limit air exchange between the inside of the structure and the outside of the structure.

56. A decontamination system for removing a substance from a subject, the decontamination system comprising:

a structure for surrounding the subject;

an inlet for allowing a gas to enter the structure;

an outlet for allowing the gas to exit the structure;

a pump for pumping the gas through the inlet, into the structure, around the subject, and out through the outlet, thereby removing at least one of substance particles and substance vapours from the subject; and a camera for monitoring the subject for any signs of ill effects arising from exposure to the substance.

57. The system of claim 56, further comprising an automated image analysis system for identifying symptoms in the subject arising from exposure to the substance.

58. The system of claim 56, further comprising:

an entrance for allowing the subject to enter the structure and an exit for allowing the subject to exit the structure; and at least one screen over the entrance and the exit to limit air exchange between the inside of the structure and the Outside of the structure.

59. A decontamination system for removing a substance from a subject, the decontamination system comprising:

a structure for surrounding the subject;

an inlet for allowing a gas to enter the structure;

an outlet for allowing the gas to exit the structure;

a pump for pumping the gas through the Inlet, into the structure, around the subject, and out through the outlet, thereby removing at least one of substance particles and substance vapours from the subject; and an automated image analysis system for identifying symptoms in the subject arising from exposure to the substance.

60. The system of claim 59, further comprising a breathing mask to supply air to the subject while (tie subject is being decontaminated.

61. The system of claim 60, further comprising a therapeutic gas provider for supplying a therapeutic gas to the subject via the breathing mask.

62. A decontamination system for removing a substance from a subject, the decontamination system comprising:

a structure for surrounding the subject;

an inlet for allowing a gas to enter the structure;

an outlet for allowing the gas to exit the structure;

a pump for pumping the gas through the inlet, into the structure, around the subject, and out through the outlet, thereby removing at least one of substance particles and substance vapours from the subject; and a breathing mask to supply air to the subject while the subject is being decontaminated.

63. A decontamination method for removing a substance from a subject, the decontamination method comprising:

surrounding a subject in a structure;

pumping gas through an inlet into the structure;

directing the gas to flow around the subject to entrain at feast one of substance particles and substance vapours , thereby decontaminating the subject;

expelling the gas, along with any entrained contaminants, from the structure through an outlet; and treating the gas in the system with an agent that neutralizes the substance.

64. The method of claim 63, wherein the step of treating includes treating the gas before the gas is pumped over the subject.

65. A decontamination method for removing a substance from a subject, the decontamination method comprising:

surrounding a subject in a structure;

pumping gas through an inlet into the structure;

directing the gas to flow around the subject to entrain at least one of substance particles and substance vapours, thereby decontaminating the subject;

expelling the gas, along with any entrained contaminants, from the structure through an outlet; and monitoring the subject with a camera for any signs of ill effects arising from exposure to the substance.

66. The method of claim 65, further comprising identifying symptoms in the subject arising from exposure to the substance with an automated image analysis system.

67. The method of claim 66, wherein the step of identifying includes identifying symptoms of miosis with the automated image analysis system.

68. The method of claim 67, further comprising supplying air to the subject with a breathing mask while the subject is being decontaminated.

69. A decontamination method for removing a substance from a subject, the decontamination method comprising:

surrounding a subject in a structure;

pumping gas through an inlet into the structure;

directing the gas to flow around the subject to entrain at least one of substance particles and substance vapours, thereby decontaminating the subject;

expelling the gas, along with any entrained contaminants, from the structure through an outlet; and identifying symptoms in the subject arising from exposure to the substance with an automated image analysis system.

70. The method of claim 69, wherein the step of identifying includes identifying symptoms of miosis with the automated image analysis system.

71. A decontamination method for removing a substance from a subject, the decontamination method comprising:

surrounding a subject in a structure;

pumping gas through an inlet into the structure;

directing the gas to flow around the subject to entrain at least one of substance particles and substance vapours, thereby decontaminating the subject;

expelling the gas, along with any entrained contaminants, from the structure through an outlet; and supplying air to the subject with a breathing mask while the subject is being decontaminated.

72. The method of claim 71, further comprising supplying a therapeutic gas to the subject via the breathing mask.

* * * * *